United States Patent
Adams

(10) Patent No.: US 10,149,731 B2
(45) Date of Patent: Dec. 11, 2018

(54) UNIVERSAL C ARM TAPE DRAPE

(71) Applicant: Ecolab USA Inc., St. Paul, MN (US)

(72) Inventor: Tammy Colvin Adams, Columbus, MS (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 15/010,600

(22) Filed: Jan. 29, 2016

(65) Prior Publication Data

US 2016/0166348 A1  Jun. 16, 2016

Related U.S. Application Data

(62) Division of application No. 12/860,209, filed on Aug. 20, 2010, now Pat. No. 9,283,041.

(60) Provisional application No. 61/235,961, filed on Aug. 21, 2009.

(51) Int. Cl.
| | | |
|---|---|---|
| *A61B 1/00* | (2006.01) | |
| *A61B 46/00* | (2016.01) | |
| *A61B 50/00* | (2016.01) | |
| *A61B 6/00* | (2006.01) | |
| *A61B 46/10* | (2016.01) | |
| *A61B 50/30* | (2016.01) | |

(Continued)

(52) U.S. Cl.
CPC ............ *A61B 46/10* (2016.02); *A61B 6/4441* (2013.01); *A61B 46/13* (2016.02); *A61B 50/30* (2016.02); *A61B 2050/314* (2016.02); *A61F 2013/15073* (2013.01); *Y10T 156/10* (2015.01); *Y10T 156/1052* (2015.01); *Y10T 428/13* (2015.01); *Y10T 428/15* (2015.01); *Y10T 428/24215* (2015.01)

(58) Field of Classification Search
CPC ....... A61B 19/02; A61B 19/08; A61B 19/081; A61B 19/087; A61B 19/088; A61B 1/00142; A61B 19/12; A61B 19/10; A61B 46/00; A61B 46/10; A61B 46/13; A61B 50/00; A61B 50/30; A61B 6/00; A61B 6/40; A61B 6/44; A61B 6/44; A61B 6/444; A61B 6/4441
See application file for complete search history.

(56) References Cited

U.S. PATENT DOCUMENTS

| | | |
|---|---|---|
| 2,491,894 A | 12/1949 | Fox |
| 2,772,886 A | 12/1956 | Parmele |

(Continued)

OTHER PUBLICATIONS

International Patent Application No. PCT/US2010/046094, International Search Report & Written Opinion dated Apr. 9, 2011, 9 pages.

(Continued)

*Primary Examiner* — Jacob T Minskey
*Assistant Examiner* — Matthew Hoover
(74) *Attorney, Agent, or Firm* — Fredrikson & Byron, P.A.

(57) ABSTRACT

A drape, such as but not limited to, a drape that can be used to cover a C arm of a medical device is provided. The drape includes material, at least one cuff and at least one adhesive strip. The material has a select property and has a select shape. The at least one cuff is formed along at least one edge of the material. The at least one cuff is configured to allow manipulation of the drape by a user. The at least one adhesive strip is configured to selectively adhere the drape to a surface to be covered by the drape.

13 Claims, 16 Drawing Sheets

(51) Int. Cl.
*A61B 46/13* (2016.01)
*A61F 13/15* (2006.01)

(56) References Cited

U.S. PATENT DOCUMENTS

| | | | | |
|---|---|---|---|---|
| 3,625,205 | A | * | 12/1971 | Madden ................ A61B 46/00 128/855 |
| 3,698,791 | A | | 10/1972 | Walchle et al. |
| 3,809,077 | A | | 5/1974 | Hansen |
| 3,835,851 | A | | 9/1974 | Villari |
| 3,952,738 | A | * | 4/1976 | Krzewinski ............ A61B 46/00 128/855 |
| 4,799,779 | A | * | 1/1989 | Mesmer ............. G02B 21/0012 206/305 |
| 5,379,703 | A | * | 1/1995 | Marshall ............... A61L 346/10 108/90 |
| 5,426,683 | A | * | 6/1995 | O'Farrell, Jr. ........ A61B 6/4405 378/193 |
| 5,506,882 | A | | 4/1996 | O'Farrell et al. |
| 5,583,909 | A | | 12/1996 | Hanover |
| 5,802,719 | A | | 9/1998 | O'Farrell et al. |
| 6,478,061 | B2 | | 11/2002 | Haberkom |
| 7,040,484 | B1 | | 5/2006 | Homra et al. |
| 7,104,201 | B2 | | 9/2006 | Comeaux et al. |
| 7,305,991 | B2 | | 12/2007 | Santilli et al. |
| 2005/0158510 | A1 | | 7/2005 | Trump |
| 2005/0247722 | A1 | | 11/2005 | Blocker |
| 2006/0161137 | A1 | | 7/2006 | Orban et al. |
| 2006/0169290 | A1 | | 8/2006 | Harris et al. |

OTHER PUBLICATIONS

European Patent Application No. 10810633.7, Extended European Search Report dated Feb. 17, 2017, 8 pages.

* cited by examiner

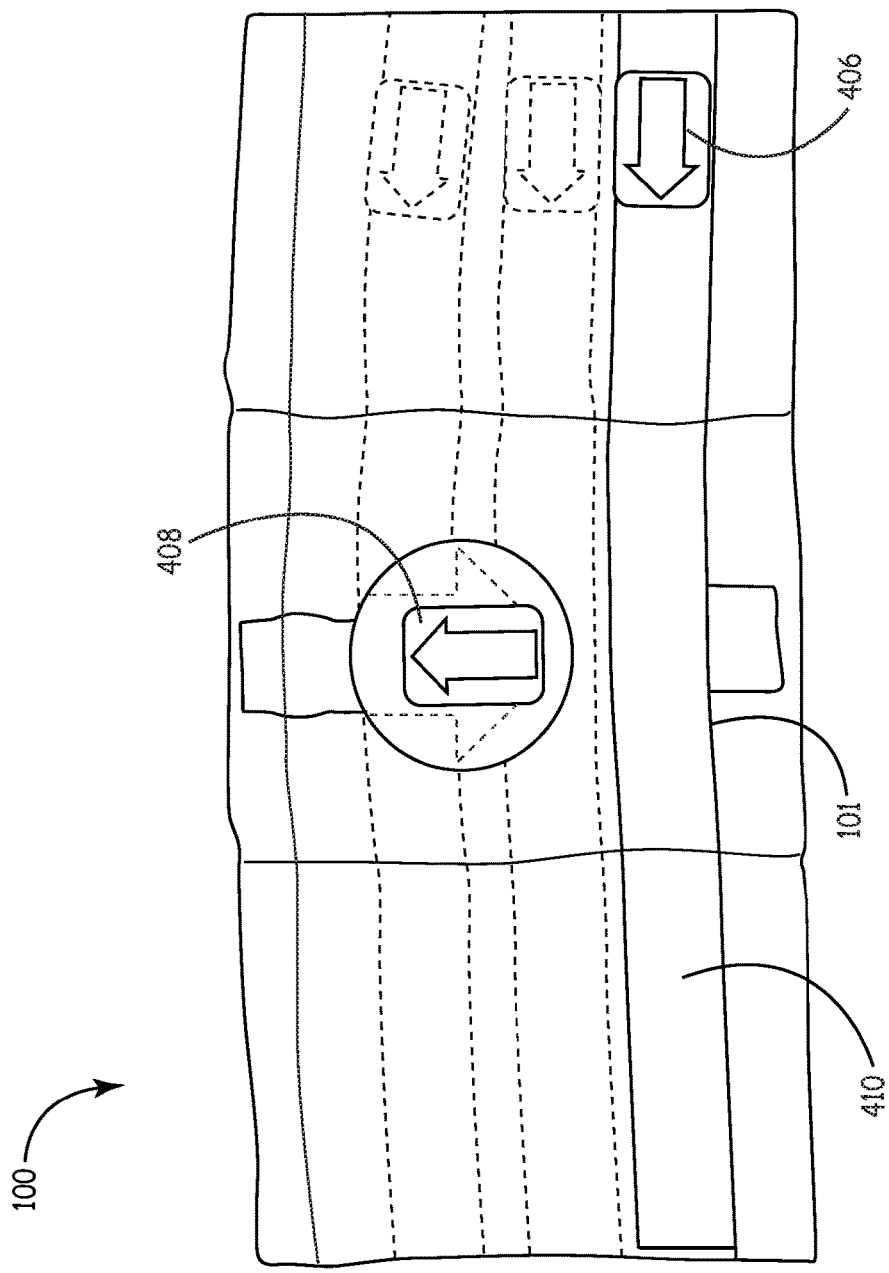

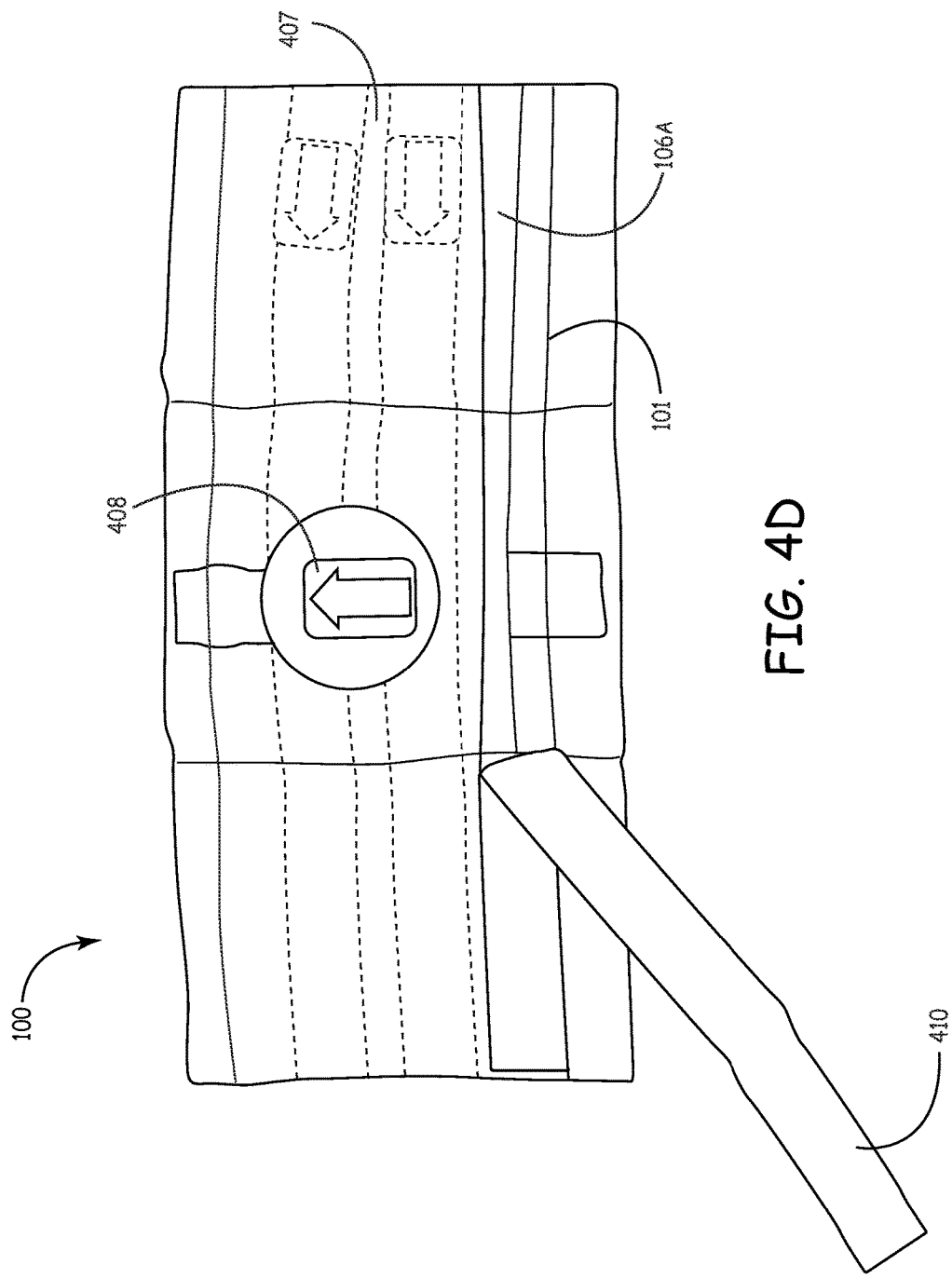

UNIVERSAL C ARM TAPE DRAPE

CROSS-REFERENCE TO RELATED APPLICATIONS

This Application claims priority to U.S. Provisional Application Ser. No. 61/235,961, filed on Aug. 21, 2009 and is a Divisional Application of U.S. application Ser. No. 12/860,209 filed on Aug. 20, 2010, same title herewith, which are both incorporated in their entirety herein by reference.

BACKGROUND

Medical equipment used in patient care facilities can be subject to contaminates such as bodily fluids. The removal of the bodily fluids from surfaces of the equipment is imperative to maintain the facilities in a relatively sterile state. This helps prevent the exposure of patients and health care personnel to undesired communicable diseases that can be spread by the bodily fluids. The use of drapes to cover the equipment can be used however, applying the drape can lead to undesired contamination.

For the reasons stated above and for other reasons stated below which will become apparent to those skilled in the art upon reading and understanding the present specification, there is a need in the art for an efficient and effective way to protect medical equipment from the exposure of bodily fluids to maintain the equipment in a sterile state.

SUMMARY OF INVENTION

The above-mentioned problems of current systems are addressed by embodiments of the present invention and will be understood by reading and studying the following specification. The following summary is made by way of example and not by way of limitation. They are merely provided to aid the reader in understanding some of the aspects of the invention.

In one embodiment, a drape is provided. The drape includes material, at least one cuff and at least one adhesive strip. The material has a select property and has a select shape. The at least one cuff is formed along at least one edge of the material. The at least one cuff is configured to allow manipulation of the drape by a user. The at least one adhesive strip is configured to selectively adhere the drape to a surface to be covered by the drape.

In another embodiment, a drape includes an impervious material layer, an end cuff, first and second side cuffs and a plurality of adhesive strips. The impervious material layer has a first end and first and second sides. The end cuff is formed along the first end of the material layer. The end cuff has an end opening configured to allow at least one hand of a user to be received in the end cuff to allow for an initial positioning of the material layer on a surface to be covered. The first side cuff is formed along the first side of the material layer and has a first opening to allow a hand of the user to be received in the first side cuff. The second side cuff is formed along the second side of the material layer and has a second opening to allow a hand of the user to be received in the second side cuff. The first and second side cuffs allow for the positioning of the material layer on the surface to be covered. The adhesive strips are configured to selectively adhere the drape to the surface to be covered by the drape.

In still another embodiment, a method of attaching a drape to a structure is provided. The method includes unfolding a first portion of the drape, placing at least one hand in an end cuff along an end of the drape in the unfolded first portion of the drape, positioning the first portion of the drape in a desired location with the at least one hand of the user in the first end cuff and pressing an adhesive strip coupled to the drape on a surface of the structure to attach the first portion of the drape to the structure.

BRIEF DESCRIPTION OF THE DRAWINGS

The present invention can be more easily understood and further advantages and uses thereof will be more readily apparent, when considered in view of the detailed description and the following figures in which:

FIGS. 4A through 4E illustrate the unfolding of a first portion of the drape of FIG. 1;

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that changes may be made without departing from the spirit and scope of the present invention. The following detailed description is, therefore, not to be taken in a limiting sense, and the scope of the present invention is defined only by the claims and equivalents thereof.

Embodiments of the present invention provide a drape that protects surfaces, such as but not limited to, surfaces of medical equipment. Embodiments of the drape protect the surfaces from getting contacted by the splattering of fluids, such as but not limited to, bodily fluids or by unsanitary objects. This prevents contaminates from getting into hard to reach areas that are difficult to clean. Embodiments of the drape also provide a quick and easy installation as well as a quick and easy clean up. Embodiments also keep a user from contaminating the user's gloves during installation. Hence, the user's gloves keep the drape sterile and the drape keeps the user's gloves sterile. In one embodiment the drape is used to cover a C shaped arm of a medical device such as an X-ray device.

Figure 1:
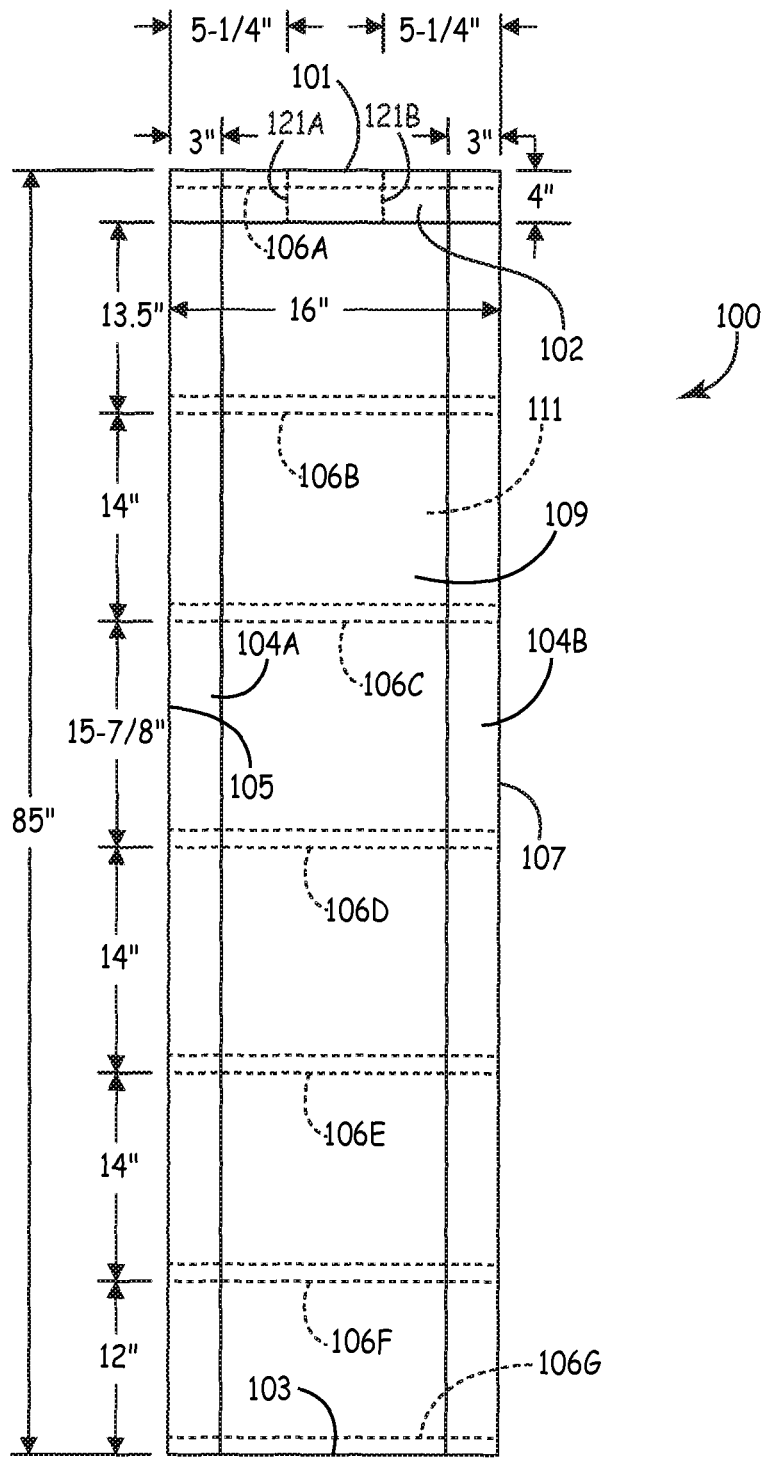
FIG. 1 is a front view of a drape of one embodiment of the present invention.

An example drape 100 of an embodiment is illustrated in FIG. 1. Drape 100 in this embodiment is generally rectangular in shape, defined by a first end edge 101, a second end edge 103, a first side edge 105 and a second side edge 107. The drape 100 further includes a first protecting side 109 and a second engaging side 111 opposite the first protecting side 109. A starting cuff 102 (or starting pocket) extends a select distance from the first end edge 101 of the drape 100 over the first protecting side 109. In one embodiment, the depth of the starting pocket is approximately in the range of 3 to 4 inches. Further, in one embodiment the depth of the starting pocket is approximately 4 inches. Further in one embodiment, the starting cuff 102 includes seals 121A and 121B. The seals 121A and 121B aid in hand placement to protect gloved hands from touching non-sterilized equipment. The embodiment of FIG. 1 further includes a first side cuff 104A (or first side pocket) and a second side cuff 104B (second side pocket). The first side cuff 104A extends a select distance from the first side edge 105 of the drape 100 over the first protecting side 109. Similarity, the second side cuff 104B extends a select distance from the second side edge 107 of the drape 100 over the first protecting side 109. In one example embodiment, the select distance that each of the first and second side cuffs 104A and 104B extend from the respective first and second sides 105 and 107 is approximately 3 inches. Hence in this example, the side cuffs 104A and 104B are approximately 3 inches deep. In another embodiment the depth of the first and second side cuffs are approximately 2 to 3 inches deep. In one embodiment, the cuffs 102, 104A and 104B are formed by folding back a select amount of material proximate the respective edges 101, 103, 105 and 107 of the material and creating folds. In one embodiment, cuffs 104A and 104B (or pockets) are formed first with cuff 102 folding over them. Cuffs 102, 104A and 104B are used to manipulate the drape 100 into position on a surface as described further below. The overall shape, length and width of the drape 100 depends on its application. In the example embodiment of FIG. 1, the length between the first end edge 101 and the second end edge 103 is generally 84⅞ inches and the width between the first side edge 105 and the second side edge 107 is generally 14 inches. These dimensions are desired for a C arm application discussed further below.

The second engaging side 111 includes a plurality of adhesive strips 106A through 106G. The adhesive strips 106A through 106G are illustrated in FIG. 1 by dashed lines. As illustrated, in this embodiment, the adhesive strips 106A through 106G extend across the width of the drape 100 between the first side edge 105 and the second side edge 107. Moreover, in this example embodiment, adhesive strip 106A is positioned proximate the first end edge 101 of the drape 100 and adhesive strip 106G is positioned proximate the second end edge 103 of the drape 100. Adhesive strips 106B through 106E are spaced between adhesive strips 106A and 106G on the second engaging side 111 of the drape 100. The adhesive strips 106A through 106G are used to adhere the second engaging side 111 of the drape 100 to a surface being protected. The spacing of the adhesive strips 106A and 106G as well as the width of the adhesive strips 106A and 106G are determined based on the application. In FIG. 1 the example spacing is indicated by given distances. An example width of the adhesive strips 106A through 106G in an embodiment is ¾ inches. Here again, the spacing of the adhesive strips 106A through 106G (as indicated in FIG. 1) and the width of the adhesive strips 106A through 106G are selected based on a universal C arm application that is further discussed below.

Drape 100 in some embodiments is made from a layer of a material that prevents the penetration of fluids. In one embodiment the drape 100 is made from a non-latex material, such as but not limited to, polyethylene. Any suitable impermeable or impervious material could be used. In other embodiments the drape is made from two or more layers of material where each material layer is select for its unique properties that are advantageous for a particular application. For example, one material layer may be made from a material that absorbs fluids while another layer is made from material that prevents penetration of fluids. In yet another embodiment, a single layer of absorbing material is used. Hence, embodiments are not limited to a specific material to form the drape 100. In one embodiment the drape 100 is made of a transparent material. In other embodiments the drape 100 is made of a select color. In further embodiments, the color selected for the drape 100 is based on a color scheme that helps identify a desired use or application of the drape 100.

Figure 2:
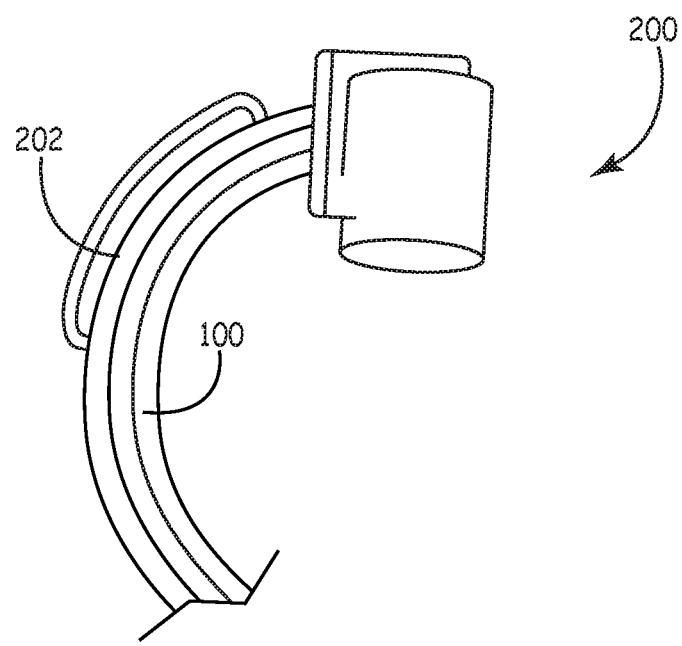
FIG. 2 is a side view of a medical imaging device with a C arm covered with a drape of FIG. 1.

One application of the drape 100 is to protect a C arm of a medical device, such as the C arm 202 of the medical device 200 of FIG. 2. The medical device 200 in this example is an imaging device such as an x-ray machine used in a patient care facility. As illustrated, the drape 100 is coupled to cover a side of the C arm 202 to protect the C arm 202 and to protect a patient who could be contacted by the C arm. The dimensions of the drape 100, as discussed above, correspond to a drape embodiment that can be used on a typical C arm 202 of a medical device 200 as illustrated in FIG. 2. It will be understood that other dimensions can be used based on the application and the present invention is not limited to specific dimensions or applications.

Figure 3A:
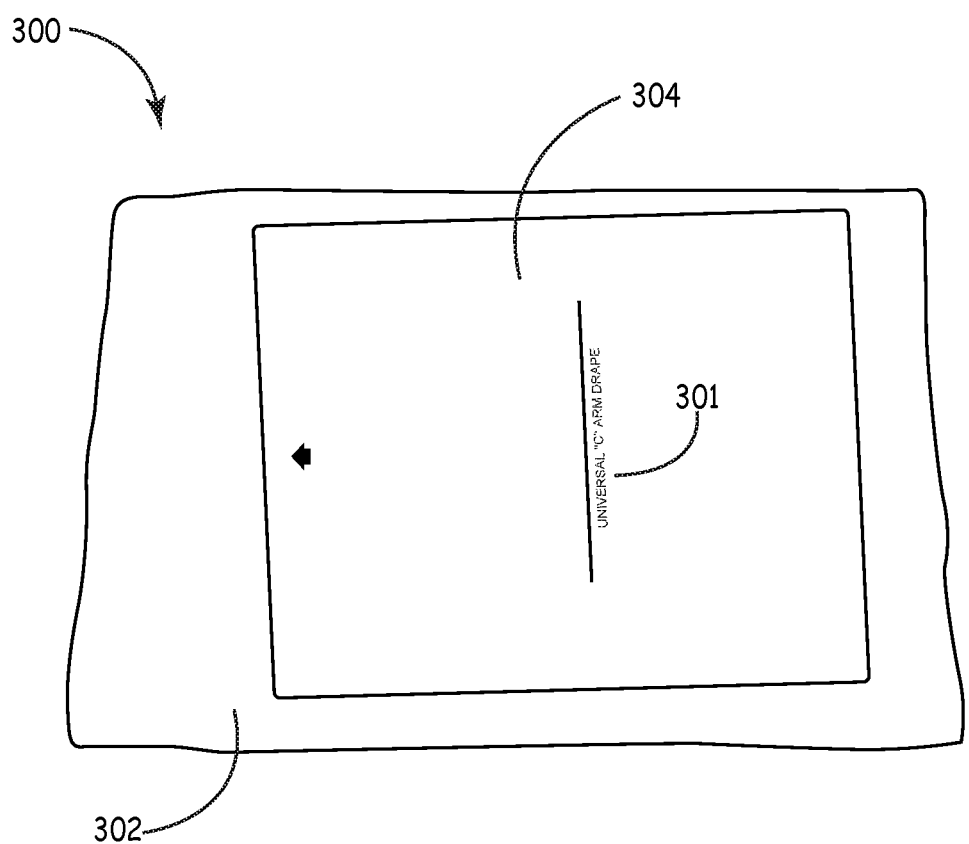
FIG. 3A is an illustration of a drape package of one embodiment of the present invention.
Figure 3B:
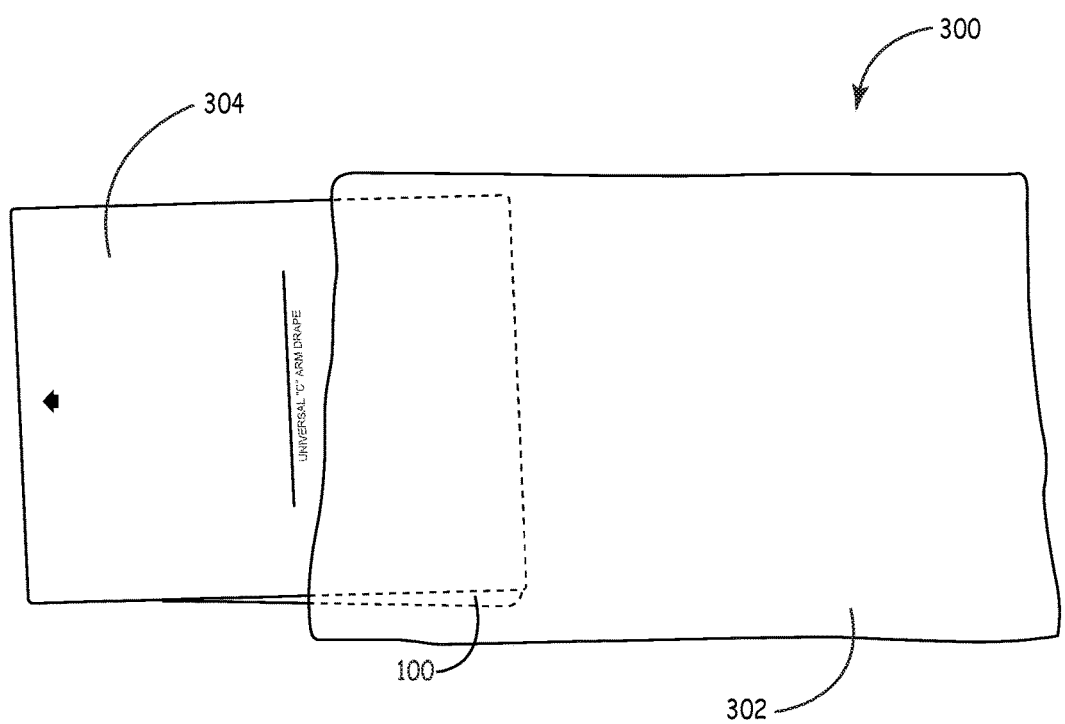
FIG. 3B is an illustration of a sleeve holding a drape being removed from the package of one embodiment of the present invention.
Figure 3C:
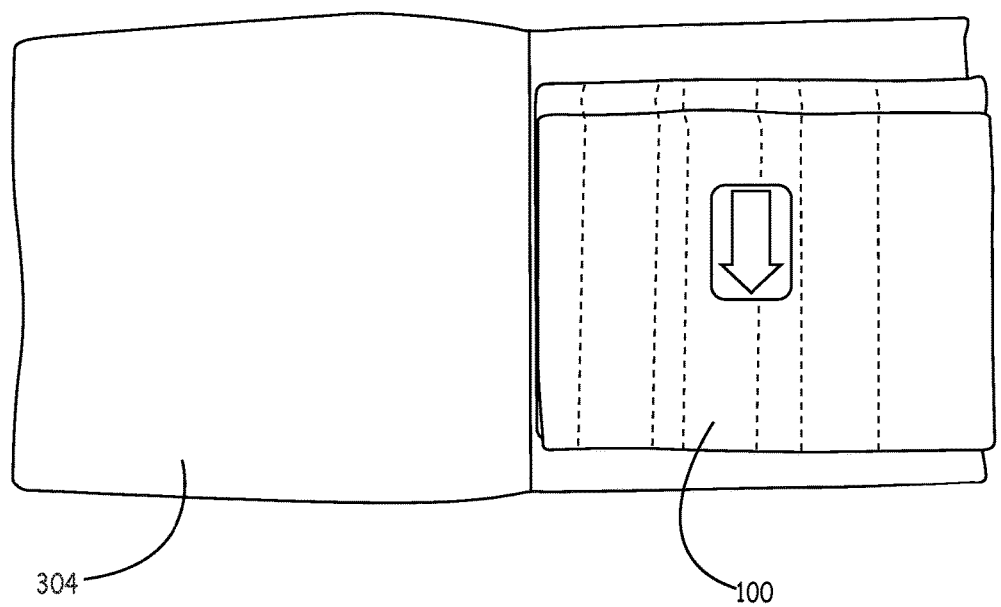
FIG. 3C is an illustration of the drape of FIG. 1 being removed from the sleeve.

FIGS. 3A through 3C illustrate a drape package 300 and the removal of the drape 100 from the package 300 in an embodiment. In FIG. 3A the drape package 300, which is hermetically sealed, is illustrated. The drape package 300 provides a sterile container for the drape 100. The drape package 300 in this embodiment includes a transparent side 302 that allows for the identification of the product (i.e. the universal "c" arm drape) to be identified. In particular, identification indicia 301 is placed on a protective sleeve 304 in the drape package 300 that can be seen through the transparent side 302 of the drape package 300. In preparing the drape package 300, a sterile drape 100 is folded and placed in a sterile sleeve 304 and then placed in the sterile drape package 300 and sealed. In removing the drape 100, an end of the drape package 300 is opened and the sleeve 304 is slid out of the package 300. This is illustrated in FIG. 3B. As illustrated in FIG. 3B, an end of the sleeve 304 having an opening to the drape is position to be the last portion of the sleeve 304 to be removed from the package 300. The sleeve 304 is then unfolded to allow access to the sterile drape 100 as illustrated in FIG. 3C. In a patient care facility, the user may use gloves in removing and applying the drape 100 to maintain a desired sterile environment.

Figure 4A:
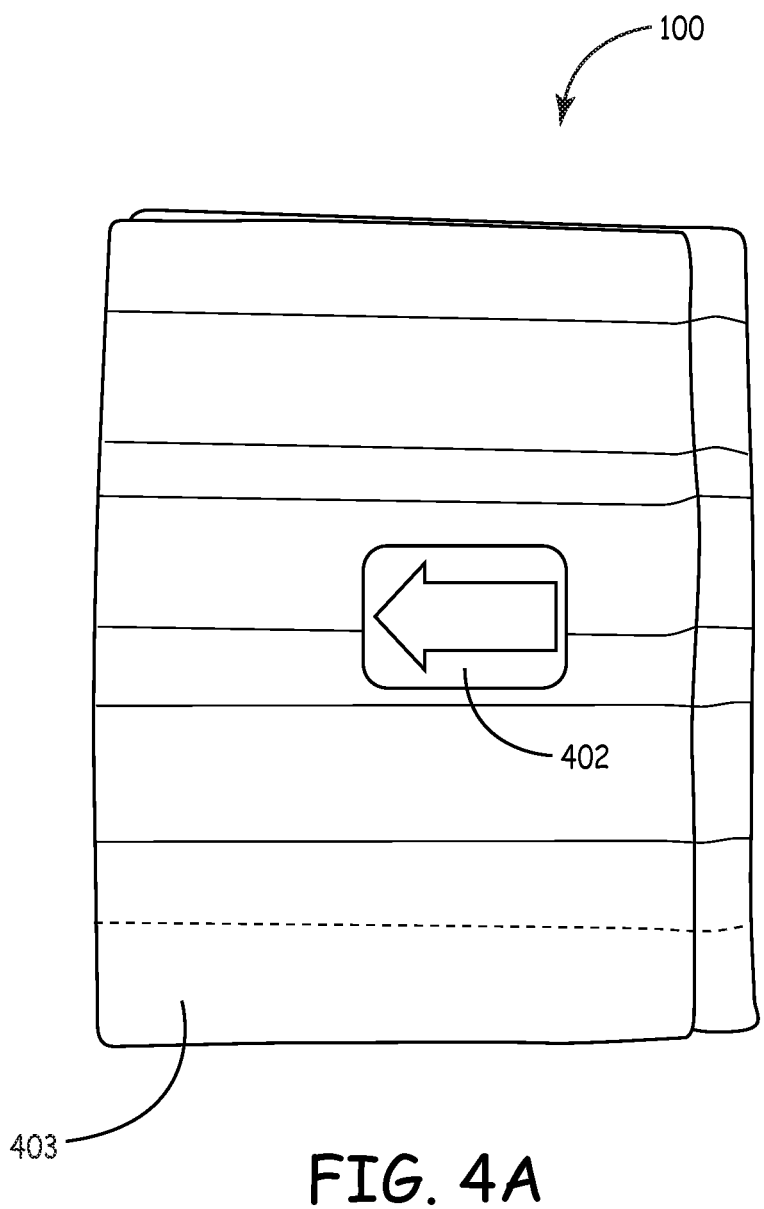
Figure 4B:
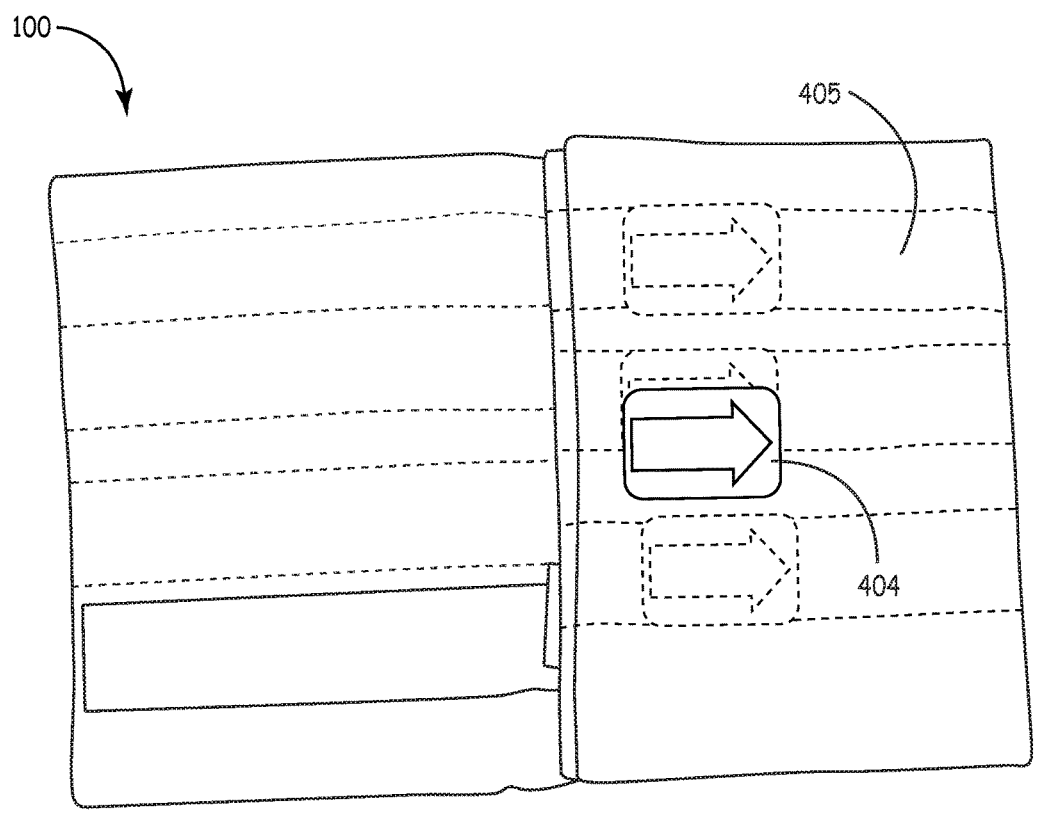

FIGS. 4A through 4K illustrate one method of applying a drape 100. Referring to FIG. 4A, an illustration of the drape 100 when removed from the drape package 300 and sleeve 304 is shown. Drape 100 has been folded in a select way that aids in attaching the drape 100 to a desired surface. Moreover, indicia have been strategically placed on the drape 100 to aid the user in unfolding and applying the drape 100. For example, the arrow indicia 402 in FIG. 4A illustrates to the user a first fold section 403 of the drape 100 to unfold in the direction of the arrow. FIG. 4B illustrates the next arrow indicia 404 on a second fold section 405 of the drape 100 that indicates the direction of the unfold. FIG. 4C illustrates the drape 100 after the first and second fold sections 403 and 405 have been unfolded. In this embodiment, the first and second fold sections 403 and 405 are unfolded along the width of the drape 100. Therefore, unfolding the first and second fold sections 403 and 405 unfolds the drape's width.

Figure 4E:
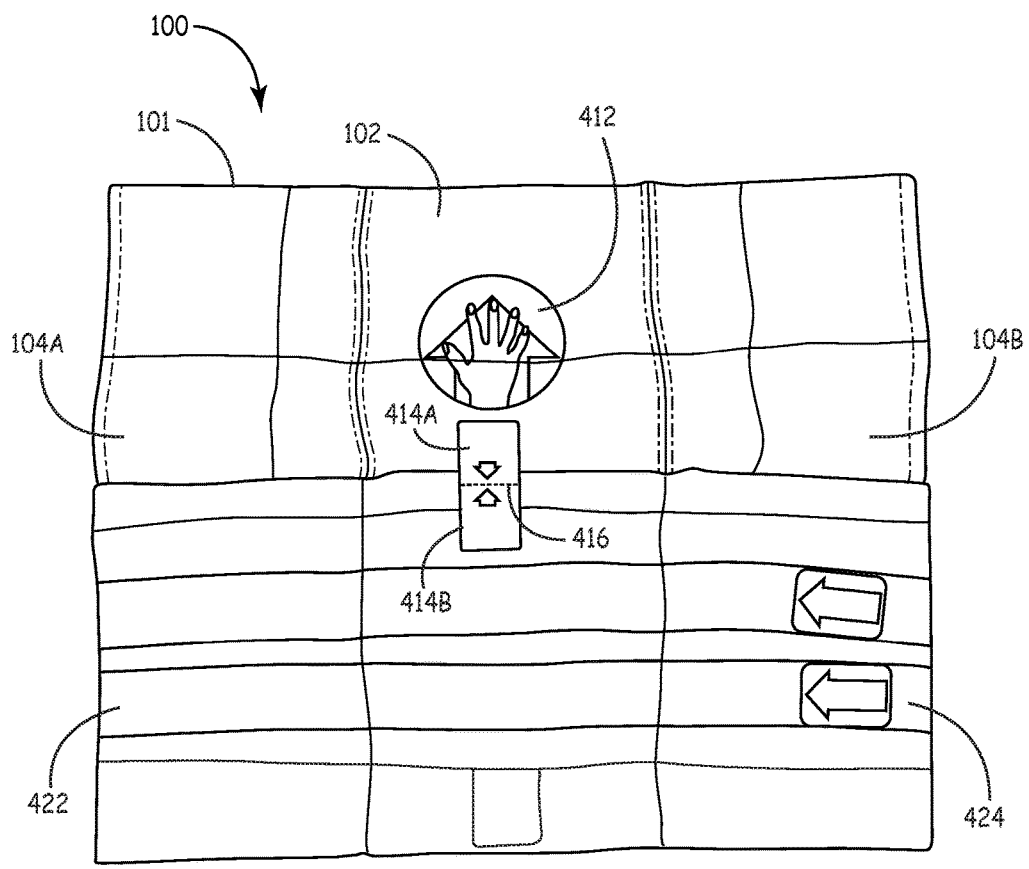
Figure 4F:
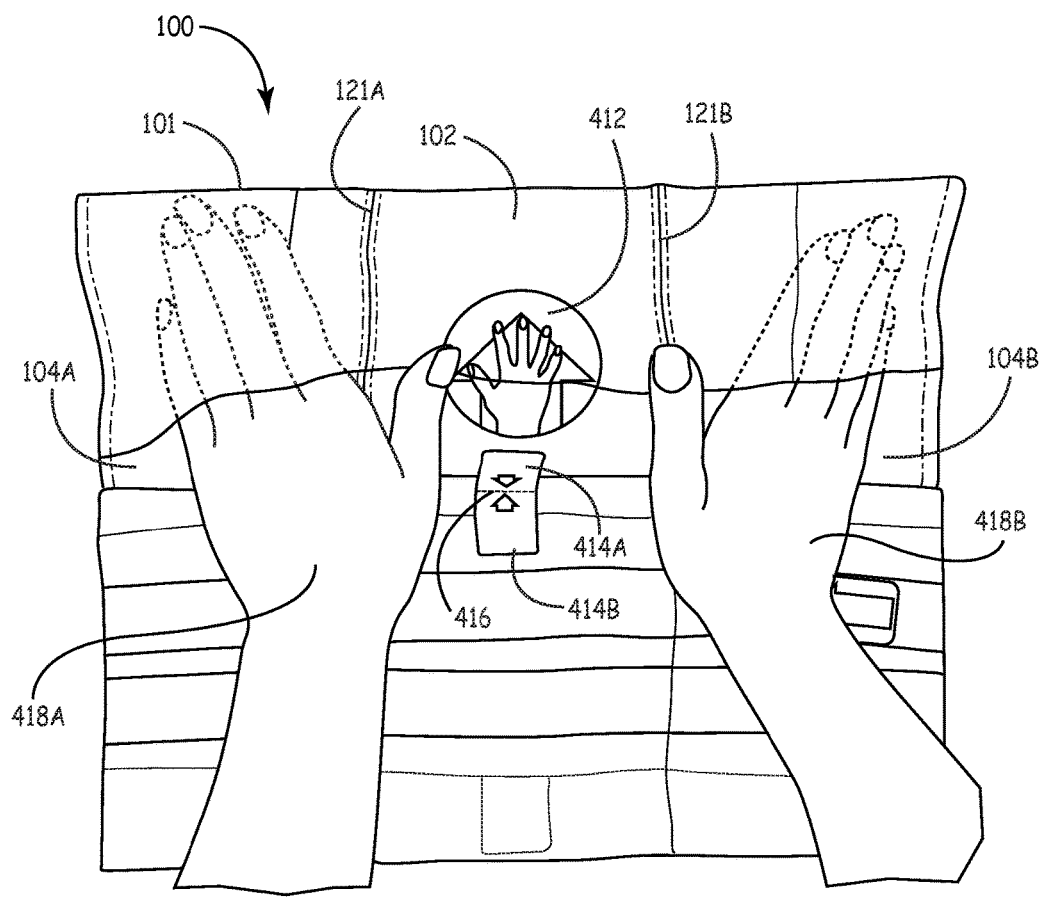
FIGS. 4F and 4G illustrate the manipulation and application of the first portion of the drape of FIG. 1.

As stated above, FIG. 4C illustrates the drape 100 after the first and second fold sections 403 and 405 have been unfolded thus arranged to contact the surface of the structure. As illustrated, indicia (two arrows 408 and 406) indicate to the user the next action to be taken. In particular, arrow 406 indicates the removal of a backing 410 that covers adhesive strip 106A that is positioned proximate the first end edge 101 of the drape 100. Referring to FIG. 4D, an illustration of the partial removal of the backing 410 from the adhesive strip 106A is shown. Once the backing is removed, a third fold section 407 is unfolded. This starts the unfolding of the folded drape 100 in the length direction as directed by arrow indicia 408. A first unfolded portion of the drape 100 is illustrated in FIG. 4E. To get to the first unfolded section illustrated in FIG. 4E, the third unfold section 407 illustrated in FIG. 4D is unfolded. As illustrated in FIG. 4E, the starting cuff 102 and side cuffs 104A and 104B are now accessible. A hand with arrow indicia 412 is used to illustrate to the user that the user's hands are to be placed in the starter cuff 102. A pair of hands 418A and 418B in the starter cuff 102 is illustrated in FIG. 4F. With the user's hands 418A and 418B in the starter cuff 102, the first end edge 101 of the drape 100 is positioned to a starting point of the surface the drape 100 is to protect. As illustrated, seals 121A and 121B in the starter cuff 102 aid in the placement of the user's hands 418A and 418B. A tape that includes tape portions 414A and 414B retains remaining folded portions of the drape 100 from unfolding while positioning and attaching the first end edge 101 of the drape 100 to the surface. Keeping the remaining folded portions in place helps control applying the drape 100 on the surface and prevents possible contamination of portions of the drape 100 not yet coupled to the surface as the application process progresses.

Figure 4G:
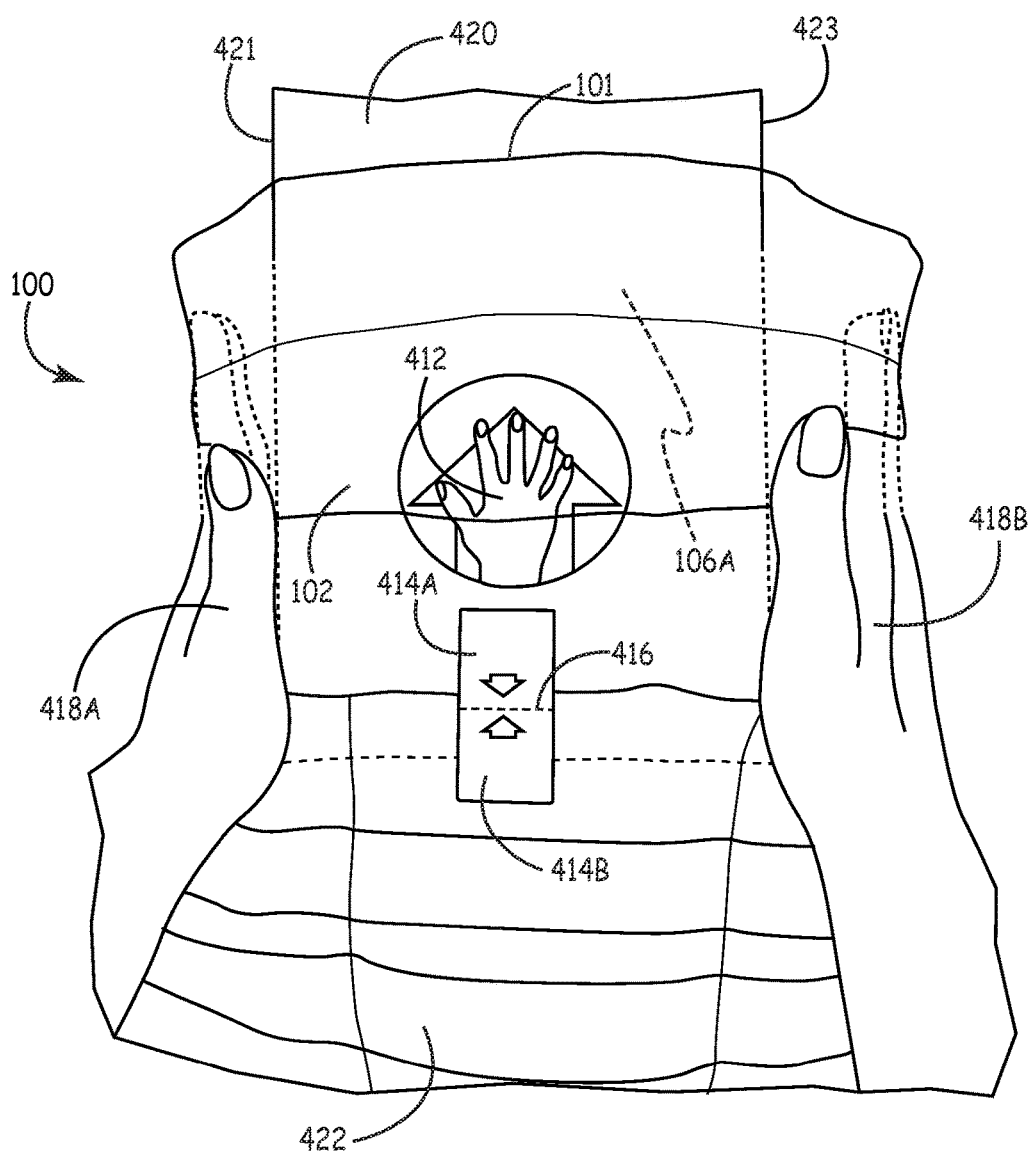

FIG. 4G illustrates the attaching of the first edge 101 of the first portion of the drape 100 on a surface of a structure. In attaching the first edge 101 to the surface, hands 418A and 418B of the user, as discussed above, are placed in the starting cuff 102 to position the first edge 101 of the drape in a desired starting location on the surface. With the user's hands 418A and 418B in the starting cuff 102 proximate a mid width portion of drape 100, the first adhesive strip 106A is pressed against a front surface 420. The user's hands 418A and 418B in this embodiment are then slid towards the side edges 105 and 107 respectfully of the drape 100 in the starting cuff 102 and the side cuffs 104A and 104B while still pressing on the first adhesive strip 106A to attach the drape 100 along opposing side surfaces 421 and 423 of the structure. Hence, the first end edge 101 of the drape 100 is attached via first adhesive strip 106A to three surfaces 420, 421 and 423 of the structure in this example. This illustrates the start of an installation of the drape 100 on a device such as a C arm discussed above.

Figure 4H:
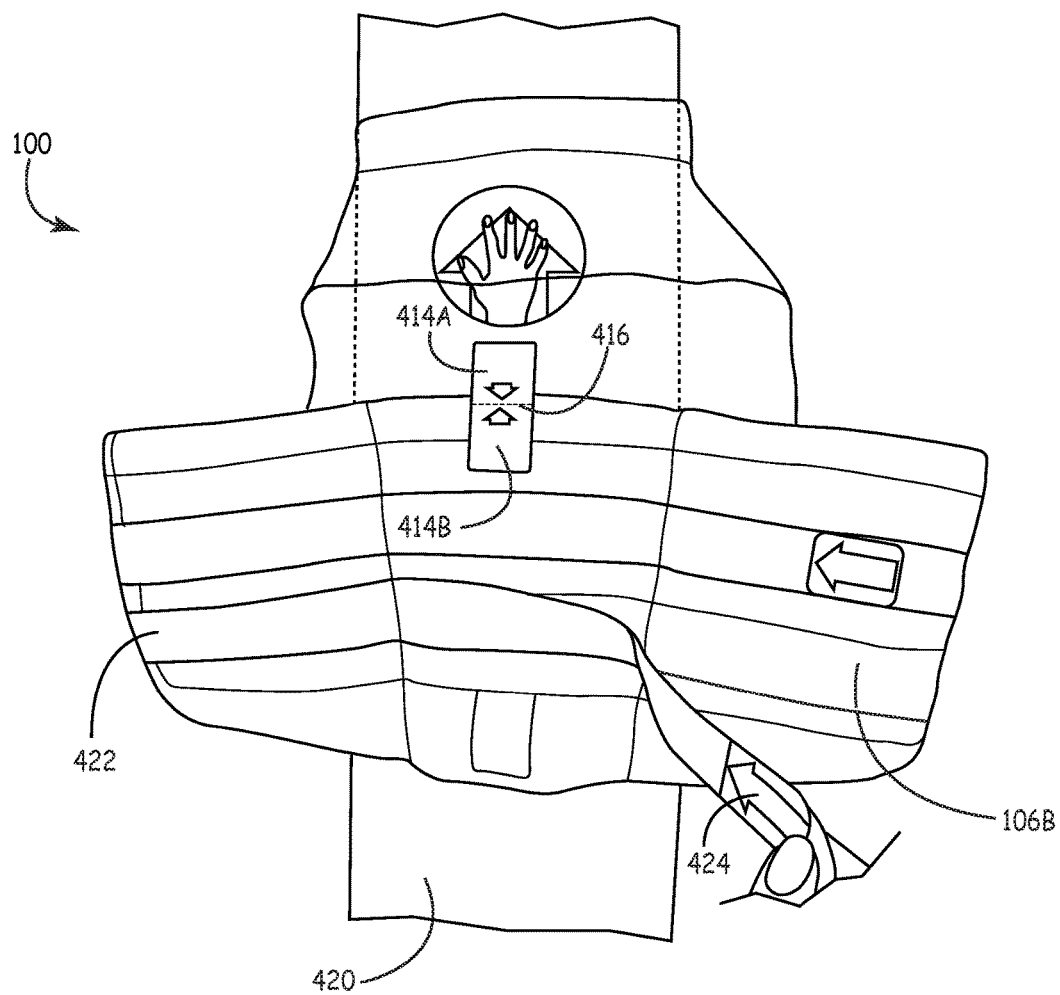
FIG. 4H through 4K illustrate the preparation, manipulation and application of another portion of the drape of FIG. 1.
Figure 4I:
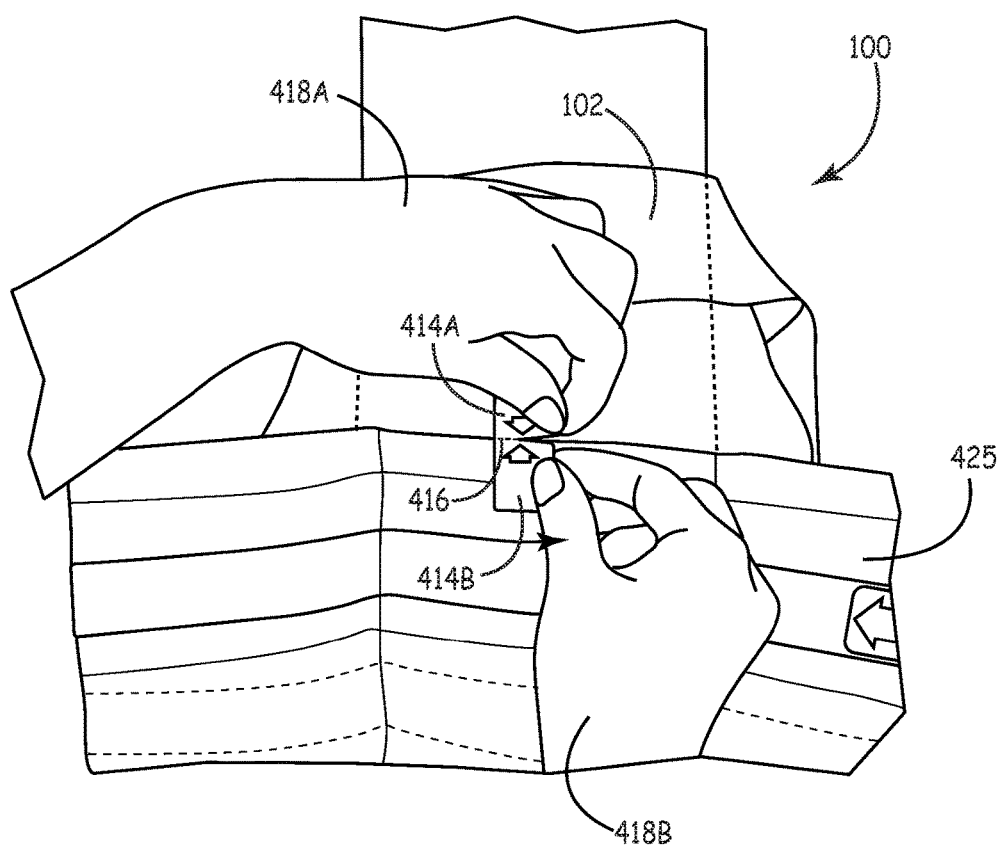
Figure 4J:
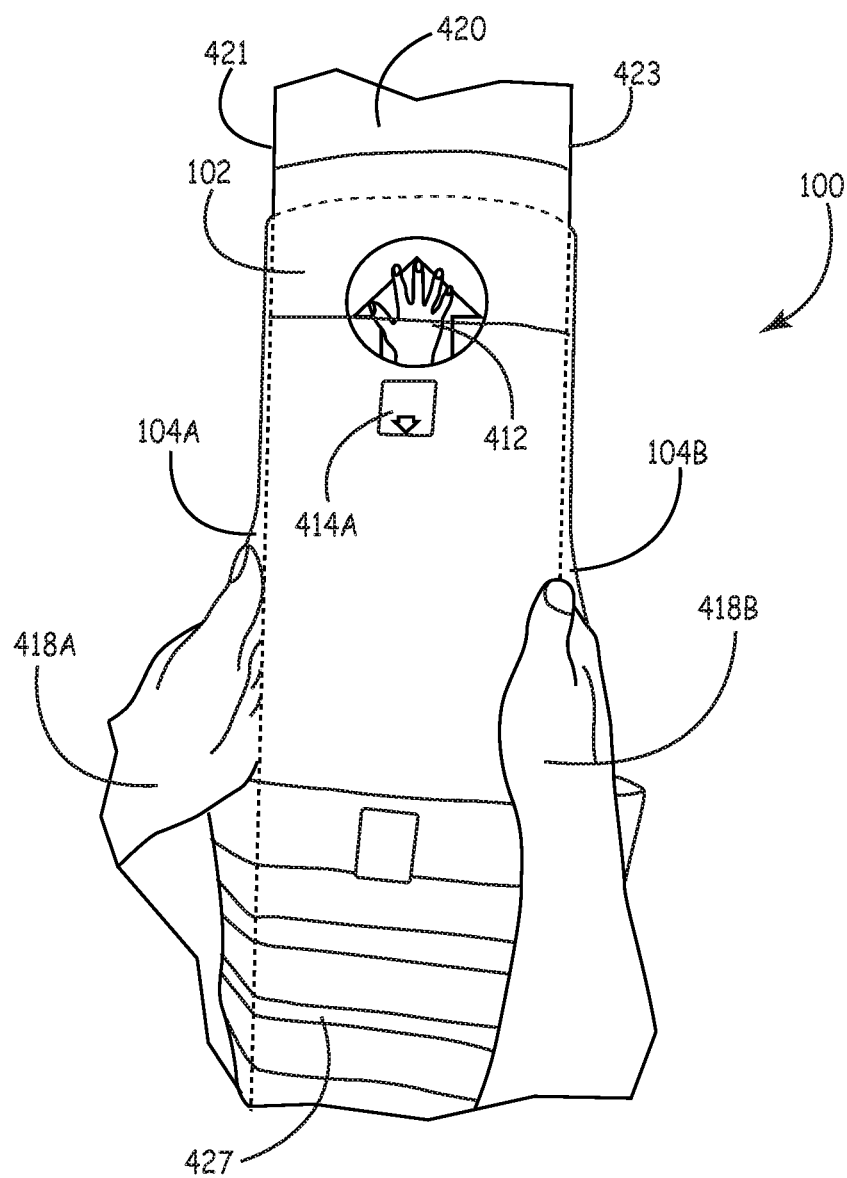
Figure 4K:
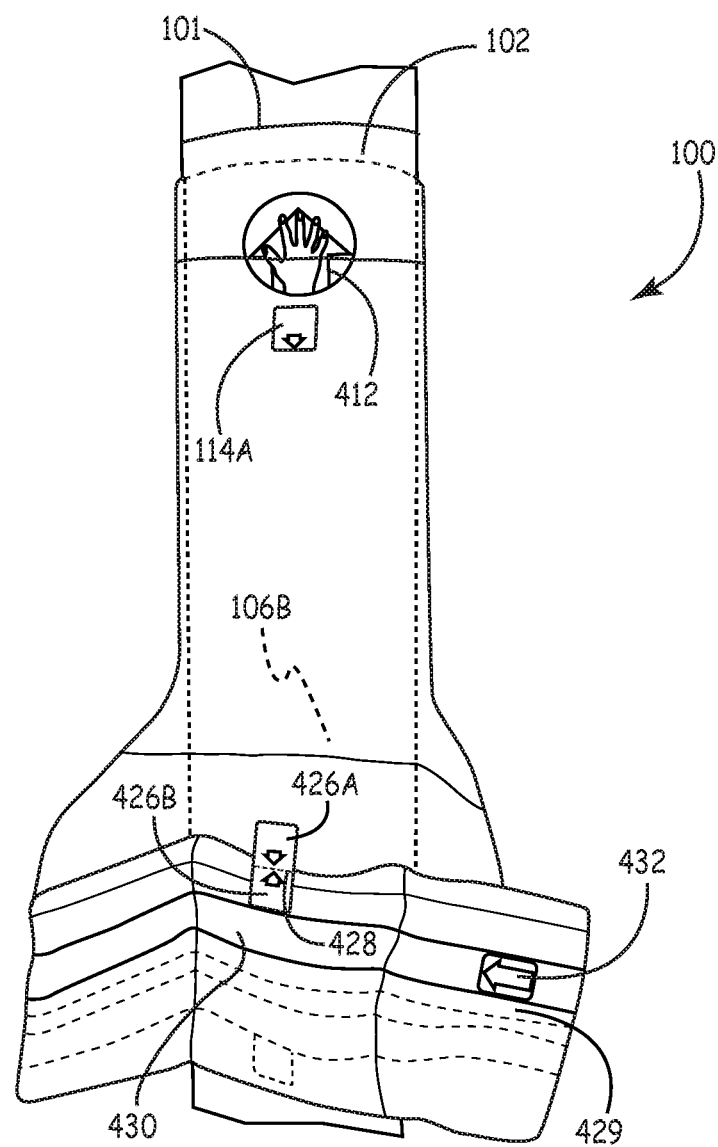

Referring to FIG. 4H, an illustration of the first portion of the drape 100 attached to a structure is illustrated. As discussed above, tape portions 414A and 414B hold the rest of the unfolded drape 100 in place to ease in the drape attachment and prevent unwanted contamination caused by the unattached portions of the drape touching contaminated surfaces. As FIG. 4H further illustrates, another arrow indicia 424 illustrates that the user is to next remove backing 422 from adhesive strip 106B. Once the backing 422 is removed from adhesive strip 106B, tape portions 414A and 414B are separated along perforation line 416 as illustrated in FIG. 4I. This allows a fourth folded section 425 to unfold as illustrated in FIG. 4J. FIG. 4J also illustrates the user's hands 418A and 418B pressing adhesive strip 106B against surfaces 420, 421 and 423 to adhere the drape to the equipment or structure. As illustrated, the user uses the side cuffs 104A and 104B to position this second portion of the drape 100 in a desired location in relation to the surface. The side cuffs 104A and 104B also allow for the easy manipulation of the drape 100 around corners of the structure. A fifth fold section 427 is then unfolded. FIG. 4K illustrates the drape 100 after the fifth fold section 427 has been unfolded. As illustrated in FIG. 4K, another tape having first and second portions 426A and 426B with a perforation line 428 there-between is used to retain a sixth folded section 429. Also, an indicia arrow 432 is used to illustrate that backing 430 is to be removed from adhesive strip 106C before the tape portions 426A and 426B are separated to unfold the sixth folded section. The process continues as described above until the all portions of the drape 100 are fully unfolded and adhered to the structure.

As illustrated, above, the drape 100 is designed and packaged so that a single user can apply it to a desired surface with minimal effort. As further discussed above, the method of applying the drape 100 also minimizes the risk of contaminating the drape when it is installed. In some embodiments the adhesive strips 106A through 106G are designed to easily disengage from the surface of the equipment or structure when the drape is being removed without leaving any residue. Although the above example embodiment is illustrated as applying to a C arm of a medical device, drapes can be designed and applied to any type of device or structure.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A method of attaching a drape to a structure, the method comprising:

placing at least one hand in a starting cuff along an end of the drape in a first portion of the drape;

positioning the first portion of the drape in a desired location with at least one hand of a user in the starting cuff;

pressing an adhesive strip coupled to the drape on a surface of the structure to attach the first portion of the drape to the structure, subsequent to pressing the adhesive strip coupled to the drape on the surface of the structure to attach the first portion of the drape to the structure:

removing the at least one hand from the starting cuff;

placing a first hand of the user in a first side cuff along a first side edge of the drape of a second portion of the drape;

placing a second hand of the user in a second side cuff along a second side edge of the drape of the second portion of the drape;

positioning the second portion of the drape in a desired location with the user's hands in the first and second side cuffs; and pressing another adhesive strip coupled to the drape on a surface of the structure to attach the second portion of the drape to the structure.

2. The method of claim 1, further comprising:
separating a tape portion to unfold the second portion from the first portion.

3. The method of claim 1, wherein the structure is a medical device.

4. The method of claim 3, wherein the medical device is an X-ray.

5. The method of claim 3, wherein the medical device has a C-shaped arm with a top surface and side surfaces,
positioning the first portion of the drape in a desired location comprises positioning the first portion of the drape over the top surface and down the side surfaces of the C-shaped arm, and
positioning the second portion of the drape in a desired location comprises positioning the second portion of the drape over the top surface and down the side surfaces of the C-shaped arm at a location longitudinally spaced from the first portion along a length of the drape.

6. The method of claim 1, further comprising, prior to placing at least one hand in a starting cuff, unfolding a first widthwise fold section of the drape and a second widthwise fold section of the drape.

7. The method of claim 1, further comprising unfolding a plurality of lengthwise fold sections of the drape, each lengthwise fold section including an adhesive strip, and attaching each of the plurality of lengthwise fold sections to the structure with the adhesive strip.

8. The method of claim 7, wherein unfolding the plurality of lengthwise fold sections of the drape comprises separating a plurality of tape portions, each tape portion holding one lengthwise fold section from remaining folded portions of the drape.

9. The method of claim 1, wherein the starting cuff has a depth ranging from approximately 3 inches to approximately 4 inches.

10. The method of claim 1, wherein the first and second side cuffs each have a depth ranging from approximately 2 inches to approximately 3 inches.

11. The method of claim 1, wherein the drape is fabricated from a non-latex polymeric material.

12. The method of claim 1, wherein the starting cuff is divided into a first starting cuff and a second starting cuff, and placing at least one hand in the starting cuff comprising placing the first hand in the first starting cuff and placing the second hand in the second starting cuff.

13. The method of claim 1, wherein the drape defines a width between a first side edge and a second side edge, and the width is approximately 14 inches.

* * * * *